(12) United States Patent
Kim et al.

(10) Patent No.: US 10,145,836 B2
(45) Date of Patent: Dec. 4, 2018

(54) APPARATUS FOR MEASURING DISSOLVED GAS AND OIL IMMERSED TRANSFORMER HAVING THE SAME

(71) Applicant: Hyundai Heavy Industries Co., Ltd., Ulsan (KR)

(72) Inventors: Jung Han Kim, Ulsan (KR); Byeong Ho Lee, Ulsan (KR); Young Keun Hur, Ulsan (KR); Byoung Woon Min, Ulsan (KR)

(73) Assignee: Hyundai Electric & Energy Systems Co., Ltd., Seoul (KR)

( * ) Notice: Subject to any disclaimer, the term of this patent is extended or adjusted under 35 U.S.C. 154(b) by 0 days.

(21) Appl. No.: 15/258,809

(22) Filed: Sep. 7, 2016

(65) Prior Publication Data

US 2017/0089879 A1 Mar. 30, 2017

(30) Foreign Application Priority Data

Sep. 25, 2015 (KR) .......................... 10-2015-0136352

(51) Int. Cl.
| | |
|---|---|
| *H01F 27/25* | (2006.01) |
| *G01N 33/28* | (2006.01) |
| *H01F 27/02* | (2006.01) |
| *H01F 27/12* | (2006.01) |

(52) U.S. Cl.
CPC ..... *G01N 33/2841* (2013.01); *G01N 33/2888* (2013.01); *H01F 27/025* (2013.01); *H01F 27/12* (2013.01)

(58) Field of Classification Search
CPC .......................................... H01F 27/00–27/36

USPC .................................. 336/65, 90, 92, 55–62
See application file for complete search history.

(56) References Cited

U.S. PATENT DOCUMENTS

| | | | | | |
|---|---|---|---|---|---|
| 4,444,040 | A | * | 4/1984 | Sakai ................. | G01N 33/2841 73/19.02 |
| 4,763,514 | A | * | 8/1988 | Naito ................. | G01N 33/2841 73/19.01 |
| 5,339,672 | A | * | 8/1994 | Spicar ................ | G01N 33/0011 210/188 |

(Continued)

FOREIGN PATENT DOCUMENTS

| | | | | |
|---|---|---|---|---|
| EP | 2546646 A1 | * | 1/2013 | ......... G01N 33/2841 |
| KR | 20-0230337 Y1 | | 4/2001 | |
| KR | 1020010086812 | | 7/2002 | |

(Continued)

*Primary Examiner* — Tuyen Nguyen
(74) *Attorney, Agent, or Firm* — Mintz Levin Cohn Ferris Glovsky and Popeo, P.C.; Peter F. Corless

(57) ABSTRACT

An apparatus for measuring dissolved gas includes a body having an internal space, a separator installation part provided in the body and having a separator allowing a dissolved gas to pass therethrough and blocking insulating oil installed therein, and a sensor installation part provided in the body and allowing a gas sensor measuring dissolved gas separated by the separator to be installed therein, wherein the separator installation part and the sensor installation part are configured in such a manner that the separator and the gas sensor are independently installed in the body or separated from the body. According to the apparatus for measuring dissolved gas, a gas sensor may be manufactured to be standardized, and excellent compatibility with respect to various types of gas sensors may be provided.

5 Claims, 4 Drawing Sheets

(56) References Cited

U.S. PATENT DOCUMENTS 6,037,592 A * 3/2000 Sunshine ........... G01N 21/3504
250/343
2011/0175623 A1 7/2011 Shrinet et al.

FOREIGN PATENT DOCUMENTS

| KR | 10-1221881 B1 | 1/2013 |
| KR | 101221881 B1 * | 1/2013 |
| KR | 1020130087476 | 9/2013 |

* cited by examiner

APPARATUS FOR MEASURING DISSOLVED GAS AND OIL IMMERSED TRANSFORMER HAVING THE SAME

CROSS-REFERENCE TO RELATED APPLICATION

This application claims benefit of priority to Korean Patent Application No. 10-2015-0136352 filed on Sep. 25, 2015 in the Korean Intellectual Property Office, the disclosure of which is incorporated herein by reference in its entirety.

BACKGROUND

1. Field

The present disclosure relates to an apparatus for measuring dissolved gas and an oil immersed transformer having the same, and more particularly, to an apparatus for measuring dissolved gas capable of measuring dissolved gas within a transformer in real time and an oil immersed transformer having the same.

2. Description of Related Art

A dissolved gas analysis method, moisture measurement method, a partial discharge measurement method, a low pressure surge test method, and the like, have been used as state diagnosis techniques for diagnosing an abnormal internal state that may occur in insulating oil of a transformer.

Among these techniques, the dissolved gas analysis method capable of measuring a degradation of insulating oil generated within a transformer as the degradation is in progress has been commonly utilized due to advantages of technically high reliability and ease in application thereof in real time.

The dissolved gas analysis method will be described hereinafter.

A transformer receives constantly uniform thermal energy as an electric coil positioned therein is used, and when a local dielectric breakdown occurs within the transformer, a partial arc discharge having a high temperature may occur.

In line with these phenomena, hydrocarbon-based insulating oil may be thermally decomposed to generate hydrogen, ($H_2$), methane ($CH_4$), acetylene ($C_2H_2$), ethylene ($C_2H_4$), and the like. In particular, in a case in which an insulating material such as an insulator, a press board, or bakelite is present in a heating portion, a gas such as carbon monoxide (CO) or carbon dioxide ($CO_2$), and the like, may also be generated.

For reference, among dissolved gases, in particular, gases such as hydrogen, methane, acetylene, ethylene, ethane, propane, and the like, are highly combustible, and are thus very critical components in undertaking safety management of a transformer.

Due to characteristics of these gases, being mostly dissolved in insulating oil, whether an error has occurred in an interior of a transformer, what kind of error it was, and in which of transformer an error occurred locally, may be diagnosed by extracting these gases and analyzing them quantitatively and qualitatively.

In order to analyze a gas dissolved in insulating oil, a method of collecting a sample of insulating oil from a transformer in operation, carrying the collected sample to an analytical laboratory, extracting gas therefrom, and analyzing the corresponding gas using gas chromatography has generally been used.

However, such an experiment laboratory analysis method has low reliability, due to general human error factors that may occur in the process of collecting a standard sample, and a great amount of time is required for analyzing the results thereof.

In order to resolve difficulty in measuring dissolved gas, a gas sensor module having an integral filter for separating oil and a gas has been developed. Such a gas sensor module may be installed in an insulating oil discharge valve, an inspection window, or a separate opening to measure an amount of dissolved gas.

However, the related art gas sensor module is difficult to standardize, and a large amount of time is required to separately manufacture sensor modules according to purposes and verifying functions thereof. Also, a sensing function may not be reliable according to materials and states of target objects, and thus, high costs may be incurred.

SUMMARY

An aspect of the present disclosure may provide an apparatus for measuring dissolved gas which facilitates replacement of a gas sensor and a filter, and an oil immersed transformer having the same.

According to an aspect of the present disclosure, an apparatus for measuring dissolved gas may include: a body having an internal space; a separator installation part provided in the body and having a separator allowing a dissolved gas to pass therethrough and blocking insulating oil installed therein; and a sensor installation part provided in the body and allowing a gas sensor measuring dissolved gas separated by the separator to be installed therein, wherein the separator installation part and the sensor installation part are configured in such a manner that the separator and the gas sensor are independently installed in the body or separated from the body.

The apparatus may further include: a connection part provided in the body and connecting the body to a casing of a transformer.

The separator may partition the internal space into an insulating oil accommodation space and a gas collection space, the connection part may be provided on the insulating oil accommodation space side, and the gas collection space may be provided on the sensor installation part side.

The apparatus may further include: a valve member coupled to the casing of the transformer to connect the casing of the transformer and the connection part, and adjusting a flow rate of insulating oil introduced into the insulating oil accommodation space.

The connection part and the sensor installation part may be provided on both ends of the body, and the separator installation part may have a pipe form branched from one side of the body.

The apparatus may further include: a cover member installed at an end of the separator installation part and supporting the separator inserted into the internal space.

The separator installation part may be provided in a direction opposite to the connection part in the body.

The sensor installation part may hermetically seal the internal space when the gas sensor is separated.

According to another aspect of the present disclosure, an oil immersed transformer may include: a casing in which insulating oil is accommodated; a discharge valve provided in the casing and discharging insulating oil; and the dissolved gas measuring apparatus connected to an outlet of the discharge valve and receiving insulating oil stored in the casing.

BRIEF DESCRIPTION OF DRAWINGS

The above and other aspects, features and other advantages of the present disclosure will be more clearly under

DETAILED DESCRIPTION

Figure 1:
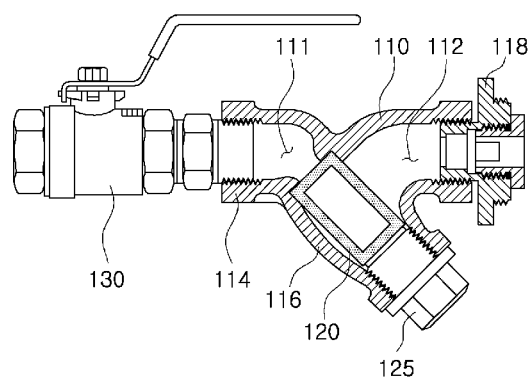
- FIG. 1 is a side cross-sectional view of an apparatus for measuring dissolved gas according to an exemplary embodiment in the present disclosure.

Hereinafter, embodiments of the present disclosure will be described as follows with reference to the attached drawings.

The present disclosure may, however, be exemplified in many different forms and should not be construed as being limited to the specific embodiments set forth herein. Rather, these embodiments are provided so that this disclosure will be thorough and complete, and will fully convey the scope of the disclosure to those skilled in the art.

Throughout the specification, it will be understood that when an element, such as a layer, region or wafer (substrate), is referred to as being "on," "connected to," or "coupled to" another element, it can be directly "on," "connected to," or "coupled to" the other element or other elements intervening therebetween may be present. In contrast, when an element is referred to as being "directly on," "directly connected to," or "directly coupled to" another element, there may be no elements or layers intervening therebetween. Like numerals refer to like elements throughout. As used herein, the term "and/or" includes any and all combinations of one or more of the associated listed items.

It will be apparent that though the terms first, second, third, etc. may be used herein to describe various members, components, regions, layers and/or sections, these members, components, regions, layers and/or sections should not be limited by these terms. These terms are only used to distinguish one member, component, region, layer or section from another region, layer or section. Thus, a first member, component, region, layer or section discussed below could be termed a second member, component, region, layer or section without departing from the teachings of the exemplary embodiments.

Spatially relative terms, such as "above," "upper," "below," and "lower" and the like, may be used herein for ease of description to describe one element's relationship to another element(s) as shown in the figures. It will be understood that the spatially relative terms are intended to encompass different orientations of the device in use or operation in addition to the orientation depicted in the figures. For example, if the device in the figures is turned over, elements described as "above," or "upper" other elements would then be oriented "below," or "lower" the other elements or features. Thus, the term "above" can encompass both the above and below orientations depending on a particular direction of the figures. The device may be otherwise oriented (rotated 90 degrees or at other orientations) and the spatially relative descriptors used herein may be interpreted accordingly.

The terminology used herein is for describing particular embodiments only and is not intended to be limiting of the present disclosure. As used herein, the singular forms "a," "an," and "the" are intended to include the plural forms as well, unless the context clearly indicates otherwise. It will be further understood that the terms "comprises," and/or "comprising" when used in this specification, specify the presence of stated features, integers, steps, operations, members, elements, and/or groups thereof, but do not preclude the presence or addition of one or more other features, integers, steps, operations, members, elements, and/or groups thereof.

Hereinafter, embodiments of the present disclosure will be described with reference to schematic views illustrating embodiments of the present disclosure. In the drawings, for example, due to manufacturing techniques and/or tolerances, modifications of the shape shown may be estimated. Thus, embodiments of the present disclosure should not be construed as being limited to the particular shapes of regions shown herein, for example, to include a change in shape results in manufacturing. The following embodiments may also be constituted by one or a combination thereof.

The contents of the present disclosure described below may have a variety of configurations and propose only a required configuration herein, but are not limited thereto.

First, an apparatus for measuring dissolved gas according to an exemplary embodiment in the present disclosure will be described with reference to FIGS. 1 through 3.

Figure 2:
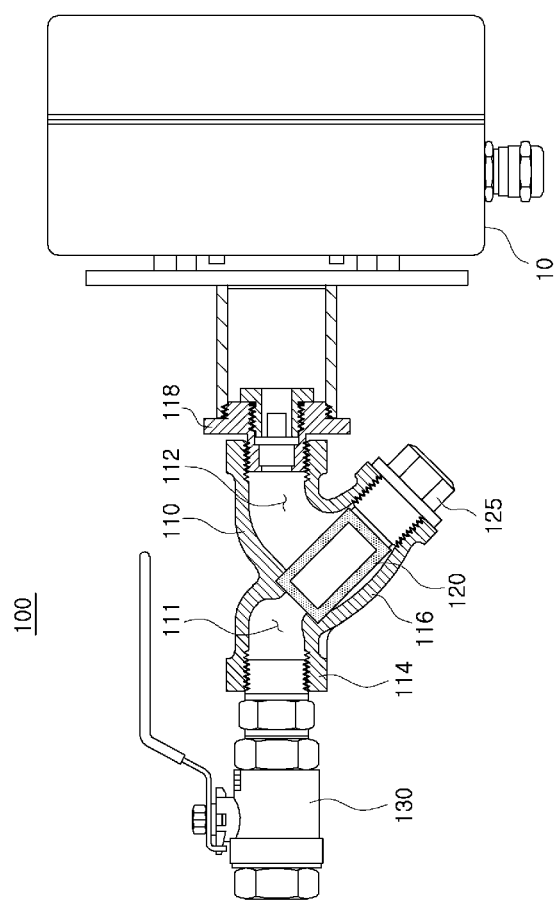
FIG. 2 is a side cross-sectional view illustrating a state in which a gas sensor is installed in the apparatus for measuring dissolved gas illustrated in FIG. 1.
Figure 3:
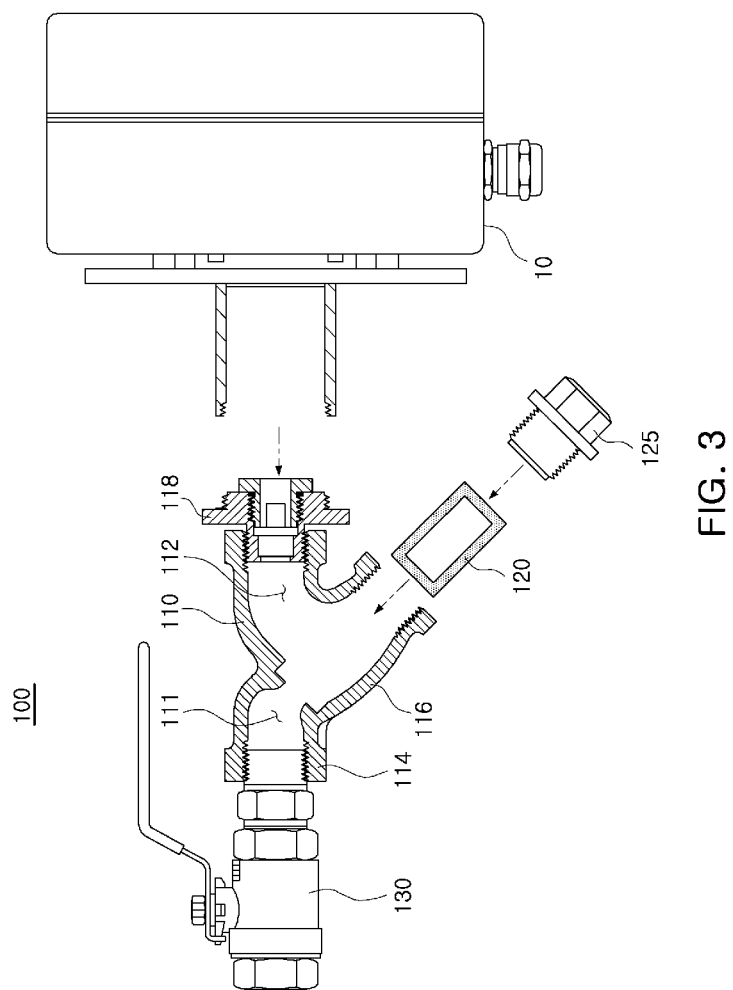
FIG. 3 is an exploded perspective view of the apparatus for measuring dissolved gas illustrated in FIG. 1.

As illustrated in FIGS. 1 through 3, an apparatus 100 for measuring dissolved gas according to an exemplary embodiment in the present disclosure may include a body 110, a separator 120, a separator installation part 116, a sensor installation part 118, a connection part 114, and a valve member 130.

The body 110 may be configured as a member having a pipe shape having an internal space. A shape and a structure of the body 110 are not particularly limited.

The separator 120 is configured to block insulating oil and allow only a dissolved gas dissolved in insulating oil to pass therethrough. The separator 120 is not particularly limited and any existing filter may be used as long as it can separate oil and a gas.

The separator 120 may be inserted into an internal space of the body 110 through the separator installation part 116 (to be described hereinafter) and removed therefrom.

In an exemplary embodiment, as illustrated in FIGS. 1 through 3, the separator 120 may have a rectangular parallelepiped shape or a cylindrical shape with both ends closed so that the separator 120 may be easily inserted into or removed from the separator installation part 116, and may be disposed as two-fold separator in a flow channel to dually perform filtering. However, the present disclosure is not limited thereto and the separator 120 may have a plate shape.

The separator 120 may partition an internal space of the body 110 into an insulating oil accommodation space 111 and a gas collection space 112. Here, insulating oil stored within a transformer may flow to the insulating oil accommodation space 111 and may be accommodated therein, and a gas dissolved in the insulating oil stored in the insulating oil accommodation space 111 may be separated by the separator 120 and collected in the gas collection space 112.

The separator installation part 116 is provided in the body 110, and has a structure in which the separator 120 may be installed.

In an exemplary embodiment, the separator installation part 116 may have a pipe shape branched from one side of the body 110, and an end thereof may be open (form an opening) to allow the separator 120 to be inserted or removed therethrough.

A cover member 125 may be installed at the end of the separator installation part 116 in order to hermetically seal the opening to prevent leakage of a dissolved gas through the opening.

The cover member 125 may hermetically seal the end of the separator installation part 116 and support the separator 120 in such a manner that the separator 120 disposed in the internal space from being released from a regular position.

For example, the cover member 125 may be threaded at an end of the separator installation part 116 so as to adapt to allow the separator 120 to have various shapes and sizes, but the present disclosure is not limited thereto.

In an exemplary embodiment, the separator installation part 116 may be provided in such a manner that an end thereof is horizontal or at least sloped in a direction opposite to the connection part 114 (to be described hereinafter) of the body 110, that is, in an outward direction of a casing 210 of the transformer. Such a structure is advantageous in that a user may remove the cover member 125 from the separator installation part 116 because the cover member 125 is disposed in an outward direction of the casing 210 of the transformer.

Also, in an exemplary embodiment, as illustrated in FIG. 1, the separator installation part 116 may extend downwardly.

Through such a structure, an internal space of the separator installation part 116 may be disposed below the gas collection space 112, and a step may be formed in a portion linking the separator installation part 116 to the gas collection space 112.

The structure of the separator installation part 116 may allow a small amount of oil leaked through the separator 120 or a periphery of the separator 120 to gather within the separator installation part 116, without flowing toward the sensor installation part 118, when the separator 120 is aged or when installation of the separator 120 is unstable.

The sensor installation part 118 may be provided in the body 110, and configured to allow a gas sensor 10 measuring dissolved gas separated by the separator 120 to be installed on the sensor installation part 118.

In an exemplary embodiment, the sensor installation part 118 may be provided at an end of the body 110 to allow the gas sensor 10 to be easily installed.

Also, the sensor installation part 118 may be configured as a joint having compatibility allowing various types of gas sensors 10 to be installed thereon.

The sensor installation part 118 may be configured to hermetically seal the gas collection space 112 so that a dissolved gas stored in the gas collection space 112 may not be leaked out when the gas sensor 10 is separated.

The connection part 114 may be provided in the body 110 and enable the body 110 to be directly or indirectly connected to the casing 210 of the transformer. Through the connection part 114, a partial amount of insulating oil within the transformer may flow to be accommodated in the insulating oil accommodation space 111.

As illustrated in FIGS. 1 through 3, in an exemplary embodiment, the connection part 114 and the sensor installation part 118 may be provided on both ends of the body 110, but the present disclosure is not limited to such a configuration.

The valve member 130 may be coupled to the casing 210 of the transformer to connect the casing 210 of the transformer and the connection part 114, and adjust a flow rate of insulating oil introduced into the insulating oil accommodation space 111.

The valve member 130 may be configured as a discharge valve discharging insulating oil from an interior of the transformer, but the present disclosure is not limited thereto and the valve member 130 may be separately provided on the casing 210 of the transformer in order to measure a dissolved gas.

In the apparatus for measuring dissolved gas according to an exemplary embodiment of the present disclosure, the separator installation part 116 and the sensor installation part 118 are separately provided in the body 110, and thus, the separator 120 and the gas sensor 10 may be independently installed in and separated from the body 110.

Thus, a user may independently replace the separator 120 and the gas sensor 10, and may easily measure various types of gases by applying various gas sensors 10 to the single separator 120.

Also, in the apparatus 100 for measuring dissolved gas according to an exemplary embodiment of the present disclosure, if necessary, the separator 120 and the cover may be removed to allow the body 110 to form an insulating oil discharge flow channel and the valve member 130 to form an insulating oil discharge valve.

Hereinafter, an oil immersed transformer 200 according to an exemplary embodiment of the present disclosure will be described with reference to FIG. 4.

Figure 4:
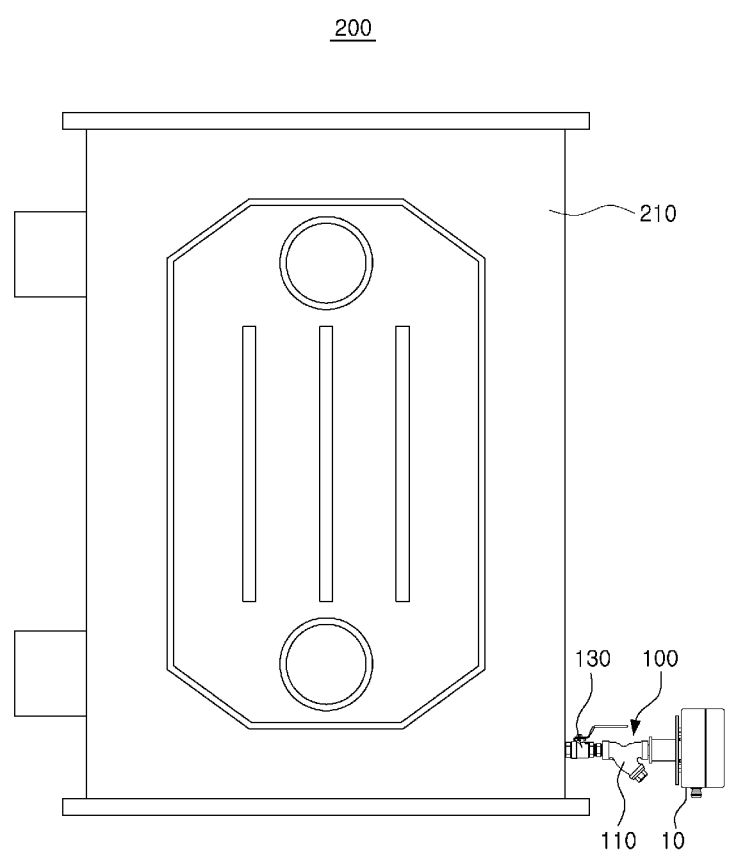
FIG. 4 is a side view of an oil immersed transformer according to an exemplary embodiment in the present disclosure.

As illustrated in FIG. 4, an oil immersed transformer 200 according to an exemplary embodiment of the present disclosure may include a casing 210 in which insulating oil is accommodated, a discharge valve provided in the casing 210 to discharge insulating oil, and a dissolved gas measuring apparatus 100 connected to an outlet of the discharge valve to receive insulating oil stored in the casing 210.

Here, the dissolved gas measuring apparatus 100 is substantially the same as the apparatus 100 for measuring dissolved gas according to an exemplary embodiment of the present disclosure described above with reference to FIGS. 1 through 3, and thus, a detailed description of components thereof will be omitted.

Also, the discharge valve may be realized as the valve member 130 included in the dissolved gas measuring apparatus 100 according to an exemplary embodiment of the present disclosure.

In this manner, since the dissolved gas measuring apparatus 100 is integrally provided on the casing 210 and various gas sensors 10 may be installed in the sensor installation part 118 of the dissolved gas measuring apparatus 100 to perform gas measurement, the oil immersed transformer 20 has excellent compatibility with respect to various gas sensors 10.

As set forth above, according to an exemplary embodiment in the present disclosure, a gas sensor may be manufactured to be standardized and excellent compatibility with respect to various types of gas sensors may be provided.

Also, according to an exemplary embodiment in the present disclosure, owing to the structural characteristics of the separator installation part and the sensor installation part which are independently formed, in the event of oil leakage due to an aged separator and unstable installation of a separator, oil is prevented from flowing to a gas sensor.

While exemplary embodiments have been shown and described above, it will be apparent to those skilled in the art that modifications and variations could be made without departing from the scope of the present invention as defined by the appended claims.

What is claimed is:
1. An apparatus for measuring dissolved gas, the apparatus comprising:

a body having an internal space;

a separator installation part provided in the body and having a separator allowing a dissolved gas to pass therethrough and blocking insulating oil, installed therein;

a sensor installation part provided in the body and allowing a gas sensor measuring dissolved gas separated by the separator to be installed therein;

a connection part provided in the body and connecting the body to a casing of a transformer; and a cover member installed at an end of the separator installation part and supporting the separator inserted into the internal space, wherein the separator installation part and the sensor installation part are configured in such a manner that the separator and the gas sensor are independently installed in the body or separated from the body, and wherein the connection part and the sensor installation part are provided on both ends of the body, and the separator installation part has a pipe form branched from one side of the body.

2. The apparatus of claim 1, wherein
the separator partitions the internal space into an insulating oil accommodation space and a gas collection space,
the connection part is provided on the insulating oil accommodation space side, and
the gas collection space is provided on the sensor installation part side.

3. The apparatus of claim 2, further comprising a valve member coupled to the casing of the transformer to connect the casing of the transformer and the connection part, and adjusting a flow rate of insulating oil introduced into the insulating oil accommodation space.

4. The apparatus of claim 1, wherein the separator installation part is provided in a direction opposite to the connection part in the body.

5. The apparatus of claim 1, wherein the sensor installation part hermetically seals the internal space when the gas sensor is separated.

* * * * *